United States Patent

Fobare et al.

Patent Number: 5,177,219
Date of Patent: Jan. 5, 1993

[54] N-PHENYL-N'-THIENYLMETHYL-BIS-DIAMINO-5-METHYLENE-1,3-DIOXANE-4,6-DIONE COMPOUNDS

[75] Inventors: William F. Fobare, Hamilton, N.J.; Donald P. Strike, St. Davids, Pa.

[73] Assignee: American Home Products Corporation, New York, N.Y.

[21] Appl. No.: 847,127

[22] Filed: Mar. 6, 1992

[51] Int. Cl.⁵ .......................... C07D 319/06
[52] U.S. Cl. .................................. 549/60
[58] Field of Search ............. 549/60, 63, 64, 65, 549/68, 69, 71, 77

[56] References Cited

U.S. PATENT DOCUMENTS

| 4,387,105 | 6/1983 | De Vries et al. | 424/322 |
| 4,387,106 | 6/1983 | De Vries et al. | 424/322 |

FOREIGN PATENT DOCUMENTS

| 0140243 | 5/1985 | European Pat. Off. | 549/77 |
| 1147759 | 4/1969 | United Kingdom | 549/61 |

OTHER PUBLICATIONS

J. Med. Chem. 29, 1131 (1986) De Vries et al.
Derwent Abstract 40365K.
Synthesis, pp. 317-320 (1989).
Chem.Abstract 71(23)112900r.

Primary Examiner—Alan L. Rotman
Assistant Examiner—Zinna N. Davis
Attorney, Agent, or Firm—Richard K. Jackson

[57] ABSTRACT

The compounds of the formula:

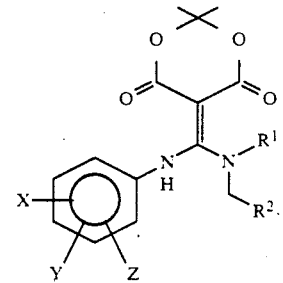

wherein X, Y and Z are, independently, hydrogen, halogen, hydroxy, nitro, cyano, carboxyl, trifluoromethyl, phenyl, amino, mono and dialkylamino, $C_1$-$C_{12}$ alkyl or $C_1$-$C_{12}$ alkoxy; $R^1$ represents hydrogen, $C_1$-$C_{18}$ saturated or unsaturated alkyl, cycloalkyl, phenyl, benzyl or substituted phenyl or substituted benzyl where the substituents are $C_1$-$C_{12}$ alkyl, or $C_1$-$C_{12}$ alkoxy: $R^2$ represents a substituted thienyl group where the substituents are, independently, the same as X, Y and Z; or a pharmaceutically acceptable salt thereof, are ACAT inhibitors.

7 Claims, No Drawings

N-PHENYL-N'-THIENYLMETHYL-BIS-DIAMINO-5-METHYLENE-1,3-DIOXANE-4,6-DIONE COMPOUNDS

BACKGROUND OF THE INVENTION

This invention relates to chemical compounds which display inhibition of Acyl-Coenzyme A: Cholestero-Acyl Transferase (ACAT). Compounds of this type may reduce cholesterol absorption and have an effect on atherosclerosis.

Atherosclerosis is the most common form of arteriosclerosis and is characterized by the build-up of phospholipids and esterified cholesterol in large and medium arteries causing them to be inelastic and thus weakened. These inelastic and occluded arteries are the most common cause of ischemic heart disease.

ACAT is an important enzyme for the intracellular esterification of cholesterol. Studies of this enzyme in cultured cells (M. S. Brown. *J. Biol. Chem.* 255 9344 (1980) has shown that increases in ACAT activity represent increases in the presence of cholesterol laden lipoproteins. Regulation of ACAT may help prevent the absorption of cholesterol in the intestinal mucosa. and may assist in the reversal of already present atherosclerotic lesions.

DESCRIPTION OF THE INVENTION

In accordance with this invention there is provided a group of diaminomethylene dioxane dione derivatives of the formula:

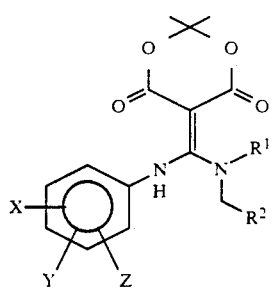

wherein

X,Y and Z are, independently, hydrogen, halogen, hydroxy, nitro, cyano, carboxyl, trifluoromethyl, phenyl, amino, mono and dialkylamino in which the alkyl groups have 1 to 6 carbon atoms, $C_1$–$C_{12}$ alkyl or $C_1$–$C_{12}$ alkoxy;

$R^1$ represents hydrogen, $C_1$–$C_{18}$ saturated alkyl, $C_2$–$C_{18}$ unsaturated alkyl, cycloalkyl of 5 to 7 carbon atoms, phenyl, benzyl or substituted phenyl or substituted benzyl where the substituents are $C_1$–$C_{12}$ alkyl, or $C_1$–$C_{12}$ alkoxy;

$R^2$ represents a substituted thienyl group where the substituents are, independently, the same as X, Y and Z; or a pharmaceutically acceptable salt thereof.

The preferred compounds are of the formula:

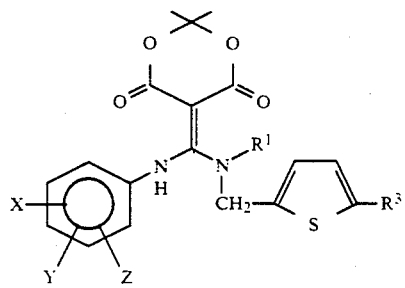

in which

X, Y and Z are, independently, hydrogen, alkyl of 1 to 6 carbon atoms, alkoxy of 1 to 6 carbon atoms, or hydroxy;

$R^1$ is alkyl of 6 to 10 carbon atoms or cycloalkyl of 5 to 7 carbon atoms;

$R^3$ is alkyl of 1 to 6 carbon atoms.

The halogen substituent referred to above may be chlorine, bromine, fluorine or iodine, fluorine being preferred. The pharmaceutically acceptable salts are derived from known inorganic or organic acids such as hydrochloric, hydrobromic, sulfuric, nitric, phosphoric, methanesulfonic, ethanesulfonic, hydroxyethanesulfonic, toluene sulfonic, naphthalenesulfonic, formic, acetic, propionic, oxalic, succinic, glycollic, lactic, malic, tartaric, citric, ascorbic, maleic, hydroxymaleic, pyruvic, phenylacetic, benzoic, para-amino benzoic, para-hydroxybenzoic, salicylic, sulfanilic acids, and the like. The most preferred values of X, Y and Z are hydrogen, alkoxy of 1 to 3 carbon atoms, hydroxy or alkyl of 1 to 4 carbon atoms. The most preferred values of $R^1$ as alkyl of 6 to 10 carbon atoms, optionally alpha branched. The most preferred values from $R^3$ are branched chain of 3 to 6 carbon atoms.

The compounds of this invention are prepared by conversion of 2,2-dimethyl-1,3-dioxane-4,6-dione to the corresponding 5-bis (methylthio) methylene derivative with carbon disulfide and methyl iodide in dimethylsulfoxide in the presence of a base such as triethylamine, followed by sequential displacement of the methylthio groups with the desired amines, thusly:

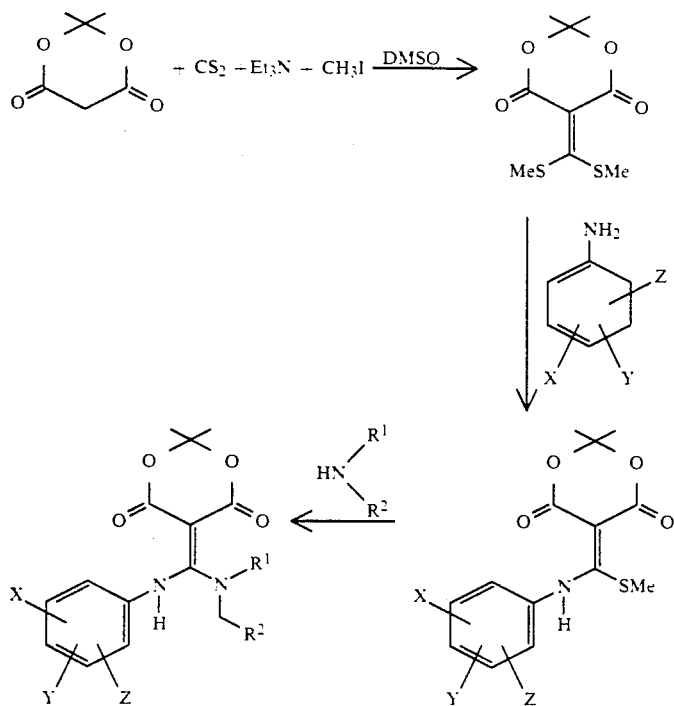

The following examples illustrate without limitation the preparation of representative compounds of this invention.

METHOD A

EXAMPLE 1

5-[[(2,4-Dimethoxyphenyl)amino][[[5-(2,2-dimethylpropyl)-2-thienyl]methyl]heptylamino]-methylene]-2,2-dimethyl-1,3-dioxane-4,6-dione

PROCEDURE 1

To a solution of 50.4 g (0.6 mol) of thiophene and 72.3 g (0.6 mol) of pivaloyl chloride in 500 mL of benzene at 0° C. was added 70.2 mL (0.6 mol) of SnCl$_4$ over a 0.75 hour period. The solution stirred at 0° C. for 0.5 hours then at room temperature for 2 hours. The reaction was quenched with 100 mL of 10% HCl and the organic layer was separated, washed twice with H$_2$O, then dried (MgSO$_4$) and the solvents were removed at reduced pressure. Distillation under vacuum (1.2 mm Hg) at 71°-73° C. yielded 67.0 g (55%) of an oil. IR (film) 3090, 2975, 1640, 1481, 1411, 1363, 1347, 1276, 1178, 1059, 908, 851 and 718 cm$^{-1}$. $^1$H NMR (200 MHz, CDCl$_3$): δ7.83 (d, 1H, J=4.0 Hz), 7.62 (dd, 1H, J=4.0, 3.8 Hz), 7.17 (dd, 1H, J=4.0, 3.8 Hz), 1.43 (s, 9H).

PROCEDURE 2

To a solution of 67.0 g (0.4 mol) of ketone from Procedure 1 (thien-2-yl, tertbutyl ketone) in 250 mL of ethanol was added 48.0 mL (1.0 mol) hydrazine. The reaction mixture was allowed to reflux for 10 days. The solvents were then removed at reduced pressure. The residue was added to 300 mL of toluene and 45 g (0.4 mol) of potassium t-butoxide was added. The reaction was heated slowly (exothermic) then taken to reflux for 3.5 hours. The reaction mixture was cooled to room temperature and added to H$_2$O. The layers were separated and the aqueous layer was extracted with diethyl ether. The combined organic layers were dried (MgSO$_4$) and the solvents removed at reduced pressure. Distillation at 16-18 mm Hg yielded 60 gms (98%) of a liquid (B.P. 86°-89° C.). IR (film) 2942, 1478, 1469, 1425, 1387, 1357, 1232, 1194, 1178, 1107, 1072, 1039, 848, 819 and 682 cm$^{-1}$. $^1$H NMR (80 MHz, CDCl$_3$): δ7.30 (m, 3H), 2.65 (s, 2H), 0.98 (s, 9H).

PROCEDURE 3

To a solution of 11.0 mL (0.14 mol) of dimethylformamide in 15 mL of dichloroethane at 0° C. was added 13.2 mL (0.14 mol) of phosphorous oxychloride over a 0.5 hour period. At 0° C. a solution 20 g (0.13 mol) of the 2-neopentylthiophene (Procedure 2) in 40 mL of ethylene dichloride was added over a 1 hour period. The reaction mixture was allowed to warm to room temperature over 0.5 hours then to reflux for 2 hours. The solution was cooled when 96 g of NaOAc.3 H$_2$O in 200 mL of H$_2$O was added and stirred for 10 minutes. The layers were separated and the aqueous layer was extracted twice with diethyl ether. The combined organic layers were washed with saturated aqueous K$_2$CO$_3$, then dried (MgSO$_4$) and concentrated at reduced pressure. Distillation of the residue at 0.6 mm Hg yielded 19.6 g (83%) of an oil (BP. 107° C.). This was used without further characterization.

PROCEDURE 4

To a solution of 19.6 g (0.11 mol) of the aldehyde from Procedure 3 (5-(2,2-dimethylpropyl)-2-thienyl-carboxaldehyde) in 70 mL of benzene was added 16.0 mL (0.11 mol) of 1-aminoheptane and a crystal of p-toluenesulfonic acid. The reaction mixture was allowed to reflux for 16 hours using a Dean-Stark trap. The solution was cooled to room temperature and the solvent was removed at reduced pressure. The residue was added to 250 mL of dry THF and HCl gas was bubbled in for 10 minutes. The mixture was cooled to 0° C. and 6.72 g (0.11 mol) of sodium cyanoborohydride in 50 mL of methanol was slowly added. The reaction mixture was allowed to stir at 0° C. for 0.5 hours then at room temperature for 17 hours. The mixture was poured into 150 mL of 0.5N NaOH and extracted twice with diethyl ether. The combined organic layers were dried (Na$_2$SO$_4$) and condensed at reduced pressure. Distillation at 0.4 mm Hg yielded 24.7 g (82%) of an oil (B.P. 153°–155° C.). IR (film) 3075, 2928, 2854, 1460, 1362, 1238, 1111, 800 and 739 cm$^{-1}$. $^1$H NMR (400 MHz, CDCl$_3$): δ6.68 (d, 1H, J=6.0 Hz), 6.54 (d, 1H, J=6.0 Hz), 3.80 (s, 2H), 2.62 (m, 4H), 1.60 (br s, 1H), 1.48 (m, 2H), 1.28 (m, 8H), 0.94 (s, 9H), 0.88 (t, 3H, J=5.8 Hz).

PROCEDURE 5

To a solution containing 2.0 g (8.05 mmol) of 5-[bis(-methylthio)methylene]-2,2-dimethyl-1,3-dioxane-4,6-dione in 40 mL of t-butanol, was added 1.23 g (8.05 mmol) of 2,4-dimethoxyaniline. The reaction mixture was allowed to stir at reflux for 24 hours. The mixture was cooled to room temperature and diluted with hexanes. The solid was filtered and used without further purification. Isolated: 2.3 g. 81% yield.

PROCEDURE 6

To a solution of 0.62 g (1.75 mmol) of the compound from Procedure 5 in 10 mL of acetonitrile was added 0.49 g (1.75 mmol) of the amine from Procedure 4, 0.31 g (1.05 mmol) of HgSO$_4$ and 0.25 mL (1.75 mmol) of triethylamine. This reaction mixture was allowed to reflux for 18 hours. The mixture was cooled, diluted with ethyl acetate and filtered through celite. The solvent was removed at reduced pressure and the residue was chromatographed on silica gel (2:1 hexanes-ethyl acetate to 1:1 hexanes-ethyl acetate) to yield 0.73 g (71%) of the title compound as a solid (mp 69°–72° C.). IR (KBr) 3420, 3210, 2955, 2860, 1702, 1634, 1571, 1512, 1456, 1390, 1367, 1312, 1208, 1160, 1084, 1038, 932, and 890 cm$^{-1}$. $^1$H NMR (400 MHz, CDCl$_3$): δ7.06 (d, 1H, J=8.72 Hz), 6.85 (d, 1H, J=3.40 Hz), 6.61 (d, 1H, J=3.40 Hz), 6.47 (d, 1H, J=2.56 Hz), 6.34 (dd, 1H, J=8.72, 2.56 Hz), 4.57 (s, 2H), 3.81 (s, 3H), 3.77 (s, 3H), 2.96 (m, 2H), 1.70 (br s, 6H), 1.55 (m, 2H), 1.17 (m, 8H), 0.95 (s, 9H), 0.84 (t, 3H, J=6.87 Hz).

Elemental analysis for C$_{32}$H$_{46}$N$_2$O$_6$S Calc'd: C, 65.50; H, 7.90; N, 4.77; Found: C, 65.73; H, 7.97; N, 4.74.

METHOD B

Example 2

5-[[[3,5-Bis(1,1-dimethylethyl)-4-hydroxyphenyl]amino][[[5-(2,2-dimethylpropyl)-2-thienyl]methyl]heptylamino]methylene]-2,2-dimethyl-1,3-dioxane-4,6-dione

PROCEDURE 1

To a solution of 6.4 g (25.8 mmol) of 5-[bis(methylthio)methylene]-2,2-dimethyl-1,3-dioxane-4,6-dione and 4.84 g (56.0 mmol) of sodium bicarbonate in 10 mL of degassed DMSO was added 10.0 g (36.0 mmol) of 3,5-di-t-butyl-4-hydroxyaniline hydrochloride in 30 mL of degassed DMSO over a 5 hour period at room temperature. Stirring was continued for an additional 19 hours. The reaction mixture was poured into cold H$_2$O and the product filtered. The solid was dried and dissolved in ethyl acetate and filtered again. The solvent was removed at reduced pressure and the residue submitted to a column chromatography on silica gel (3:1 to 2:1 hexane-ethyl acetate) to yield 9.8 g (90%) of a solid that was used without further purification.

PROCEDURE 2

To a solution of 0.58 g (2.08 mmol) of the amine synthesized in Method A, Procedure 4 in 20 mL of CH$_3$CN was added 0.84 g of the compound from Method B, Procedure 1, 0.29 g (0.99 mmol) of HgSO$_4$ and 0.2 g (1.98 mmol) of triethylamine. The solution was allowed to reflux for 18 hours. The reaction mixture was cooled to room temperature, diluted with ethyl acetate and filtered through celite. The solvents were removed at reduced pressure and the residue was chromatographed on silica gel (3:1 hexanes-ethyl acetate to 1:1 hexanes-ethyl acetate) to yield after recrystallization (hexanes-ethyl acetate) 1.0 g (77%) of the title compound as a pale yellow solid (mp 178°–179° C.). IR (KBr) 3405, 2950, 2859, 1696, 1623, 1573, 1462, 1432, 1383, 1361, 1233, 1204, 1115, 1088, 931 and 800 cm$^{-1}$. $^1$H NMR (400 MHz, CDCl$_3$): δ6.93 (s, 2H), 6.85 (d, 1H, J=3.32 Hz), 6.59 (d, 1H, J=3.32 Hz), 5.23 (br s, 1H), 4.56 (s, 2H), 3.05 (m, 2H), 2.62 (s, 2H), 1.72–1.55 (m, 8H), 1.38 (s, 18H), 1.34–1.09 (m, 8H), 0.94 (s, 9H), 0.85 (t, 3H, J=6.9 Hz).

Elemental analysis for C$_{38}$H$_{48}$N$_2$O$_5$S Calc'd: C, 69.65; H, 8.93; N, 4.28; Found: C, 69.76; H, 9.05; N, 4.12.

EXAMPLE 3

5-[[(2,4-Dimethoxyphenyl)amino][[[5-(2,2-dimethylpropyl)-2-thienyl]methyl](1-methylhexyl)-amino]methylene]-2,2-dimethyl-1,3-dioxane-4,6-dione This compound was synthesized using the same methodology as in Method A except 2-aminoheptane was substituted for 1-aminoheptane to yield 1.37 g (81%) of a white powder (mp 152°–153° C.).

Elemental analysis for C$_{32}$H$_{46}$N$_2$O$_6$S Calc'd: C, 65.50; H, 7.90; N, 4.77; Found: C, 65.88; H, 8.00; N, 4.66.

EXAMPLE 4

5-[[[3,5-Bis(1,1-dimethylethyl)-4-hydroxyphenyl]amino][[[5-(2,2-dimethylpropyl)-2-thienyl]methyl](1-methylhexyl)amino]methylene]-2,2-dimethyl-1,3-dioxane-4,6-dione This compound was synthesized using the same methodology as in Method B except 2-aminoheptane was substituted for 1-aminoheptane in Method A to yield 2.0 g (85%) of a white powder (mp 184°–185° C.).

Elemental analysis for C$_{38}$H$_{58}$N$_2$O$_5$S Calc'd: C, 69.69; H, 8.92; N, 4.28; Found: C, 69.56; H, 8.83; N, 4.34.

EXAMPLE 5

5-[[[Cyclohexyl-[5-(2,2-dimethylpropyl)-2-thienyl]methyl]amino]-[(2,4-dimethoxyphenyl)amino]-methylene]-2,2-dimethyl-1,3-dioxane-4,6-dione This compound was synthesized using the same methodology as in Method A except cyclohexylamine was substituted for 1-aminoheptane to yield 1.21 g (71%) of an off-white powder (mp 143°–145° C.).

Elemental analysis for C$_{31}$H$_{42}$N$_2$O$_6$S Calc'd: C, 65.24; H, 7.42; N, 4.91; Found: C, 65.61; H, 7.57; N, 4.60.

The ability of the compounds of this invention to inhibit acyl-coenzyme A: cholesterol acyltransferase was established by initially showing that they inhibited intracellular cholesterol esterification by subjecting them to the standard experimental test procedure of Ross et al., J. Biol. Chem. 259 815 (1984).

The results of these studies are as follows:

TABLE

| Compound | In Vitro % Inhibition (Conc., μM) | IC$_{50}$ (μM) |
| --- | --- | --- |
| 1 | 94(25) | 2.96 |
| 2 | — | 0.70 |
| 3 | 97(25) | — |
| 4 | — | 0.64 |
| 5 | 95(25) | — |

From these data, the ability of the compounds to inhibit ACAT is clearly established. Hence, the compounds of this invention are useful in the treatment of those disease states which are amenable to treatment by reduction of the rate of cholesterol esterification, the rate of accumulation and deposits of cholesteryl esters on arterial walls and the rate of formation of atheromatous lesions. As such, the antiatherosclerotic agents of this invention may be administered to a mammal in need of intracellular cholesteryl ester concentration reduction orally or parenterally in an amount sufficient to inhibit ACAT catalysis of cholesterol esterification.

The compounds of this invention may be administered by themselves or in combination with pharmaceutically acceptable liquid or solid carriers. Oral administration in conventional formulations as tablets, capsules, powders, or suspensions is preferred.

A solid carrier can include one or more substances which may also act as flavoring agents, lubricants, solubilisers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both of pharmaceutically acceptable oils or fats. The liquid carrier can contain other suitable pharmaceutical additives such as solubilisers, emulsifiers, buffers, preservatives, sweeteners, flavoring agents, suspending agents, thickening agents, colors, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g., glycols) and their derivatives, and oils (e.g. fractionated coconut oil and arachis oil). For parenteral administration, the carrier can also be an oil ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular intraperitoneal or subcutaneous injection. Sterile solutions can also be administrated intravenously. When the compound is orally active, it can be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific hypercholesterolemic/atherosclerotic condition must be subjectively determined by the attending physician. The variables involved include the extent of the disease state, size, age and response pattern of the patient.

What is claimed is:

1. A compound of the formula:

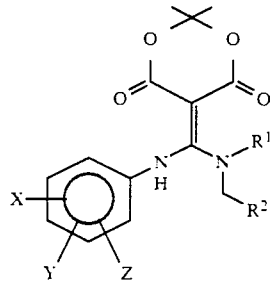

wherein

X, Y and Z are, independently, hydrogen, halogen, hydroxy, nitro, cyano, carboxyl, trifluoromethyl, phenyl, amino, mono and dialkylamino in which the alkyl groups have 1 to 6 carbon atoms, $C_1$-$C_{12}$ alkyl or $C_1$-$C_{12}$ alkoxy;

$R^1$ represents hydrogen, $C_1$-$C_{18}$ saturated alkyl, $C_2$-$C_{18}$ unsaturated alkyl, cycloalkyl of 5 to 7 carbon atoms, phenyl, benzyl or substituted phenyl or substituted benzyl where the substituents are $C_1$-$C_{12}$ alkyl, or $C_1$-$C_{12}$ alkoxy;

$R^2$ represents a substituted thienyl group where the substituents are, independently, the same as X, Y and Z;

or a pharmaceutically acceptable salt thereof.

2. A compound of Claim 1 of the formula:

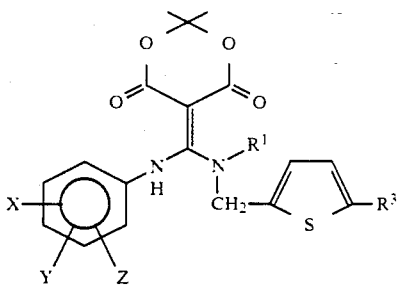

in which

X, Y and Z are, independently, hydrogen, alkyl of 1 to 6 carbon atoms, alkoxy of 1 to 6 carbon atoms, or hydroxy;

$R^1$ is alkyl of 6 to 10 carbon atoms or cycloalkyl of 5 to 7 carbon atoms;

$R^3$ is alkyl of 1 to 6 carbon atoms.

3. A compound of Claim 1 which is 5-[[(2,4-dimethoxyphenyl)amino][[[5-(2,2-dimethylpropyl)-2-thienyl]methyl]heptylamino]methylene]2,2-dimethyl-1,3-dioxane-4,6-dione.

4. A compound of Claim 1 which is 5-[[[3,5-bis(1,1-dimethylethyl)-4-hydroxyphenyl]amino][[[5-(2,2-dimethylpropyl)-2-thienyl]methyl]heptylamino]methylene]-2,2-dimethyl-1,3-dioxane-4,6-dione.

5. A compound of Claim 1 which is 5-[[(2,4-dimethoxyphenyl)amino][[[5-(2,2-dimethylpropyl)-2-thienyl]methyl](1-methylhexyl)amino]methylene]-2,2-dimethyl-1,3-dioxane-4,6-dione.

6. A compound of Claim 1 which is 5-[[[3,5-bis(1,1-dimethylethyl)-4-hydroxyphenyl]amino][[[5-(2,2-dimethylpropyl)-2-thienylmethyl](1-methylhexyl)amino]methylene]-2,2-dimethyl-1,3-dioxane-4,6-dione.

7. A compound of Claim 1 which is 5-[[[cyclohexyl-[5-(2,2-dimethylpropyl)-2-thienyl]methyl]amino]-[(2,4-dimethoxyphenyl)amino]methylene]-2,2-dimethyl-1,3dioxane-4,6-dione.

* * * * *